United States Patent [19]
Pitha

[11] Patent Number: 4,727,064
[45] Date of Patent: Feb. 23, 1988

[54] PHARMACEUTICAL PREPARATIONS CONTAINING CYCLODEXTRIN DERIVATIVES

[75] Inventor: Josef Pitha, Baltimore, Md.

[73] Assignee: The United States of America as represented by the Department of Health and Human Services, Washington, D.C.

[21] Appl. No.: 738,749

[22] Filed: May 29, 1985

Related U.S. Application Data

[63] Continuation-in-part of Ser. No. 603,839, Apr. 25, 1984, Pat. No. 4,596,795.

[51] Int. Cl.$^4$ .................. A61K 31/70; C08B 37/16
[52] U.S. Cl. ........................... 514/58; 106/210; 536/103; 514/965; 514/971
[58] Field of Search .............. 536/103; 106/210; 514/58, 971, 965

[56] References Cited

U.S. PATENT DOCUMENTS

| | | | |
|---|---|---|---|
| 2,827,452 | 3/1958 | Schlenk et al. | 514/58 |
| 3,420,788 | 1/1969 | Solms | 536/103 |
| 3,453,257 | 7/1969 | Parmerter et al. | 536/103 |
| 3,453,259 | 7/1969 | Parmerter et al. | 536/103 |
| 3,459,731 | 8/1969 | Gramera et al. | 536/103 |
| 4,380,626 | 4/1983 | Szejtli et al. | 536/103 |
| 4,383,992 | 5/1983 | Lipari | 514/174 |
| 4,524,068 | 6/1985 | Szejtli et al. | 514/58 |
| 4,555,504 | 11/1985 | Jones | 536/103 |
| 4,596,795 | 6/1986 | Pitha | 514/58 |

FOREIGN PATENT DOCUMENTS

| | | | |
|---|---|---|---|
| 57-130914 | 8/1982 | Japan . | |
| 1453801 | 10/1976 | United Kingdom | 536/103 |
| 2104907 | 3/1983 | United Kingdom | 536/103 |

OTHER PUBLICATIONS

Fenyvesi et al., Water-Soluble Cyclodextrin Polymers-ing I. Int. Symposium on Cyclodextrins, p. 345 (Budapest, 1981).
Maeno, Liquid Crystal Element and Its Use, Chem. Abstracts, 87: 144000u (1977).
Kyowa Hakko Kogyo Co., Inclusion Compound of Medroxyprogesterone . . . and B-Cyclodextrin, Chem. Abstracts, 98: 8163z (1982).
Uekama et al., Inclusion Complexation of Steroid Hormones with Cyclodextrins . . . , Chem. Abstracts, 96: 149046j (1982).
J. Szejtli, "Cyclodextrins and Their Inclusion Complexes", Akademiai Kiado, Budapest, 1982, pp. 204–232.
J. Pitha, L. Szente and J. Szejtli, "Molecular Encapsulation of Drugs by Cyclodextrins and Congeners", in Controlled Drug Deliver, S. D. Bruck, ed., CRC Press, 1983, pp. 125–148.
M. L. Bender and M. Komiyama, "Cyclodextrin Chemistry," Springer-Verlag, Berlin, 1978, pp. 29–32.
E. Fenyvesi et al, Chem. P'- m. Bull., 32:665, 1984.
E. Fenyvesi et al, Che. n. Bull., 32:670, 1984.

Primary Examiner—Ronald W. Griffin
Attorney, Agent, or Firm—John S. Roberts, Jr.

[57] ABSTRACT

The invention comprises pharmaceutical preparations consisting generally of a drug with a substantially low water solubility and an amorphous, water-soluble cyclodextrin-based mixtures. In these preparations a stable amorphous state can be achieved. This improves the dissolution properties of the drug and hence its absorption by the body. The required cyclodextrin-based mixtures were prepared from α-, β-, or γ-cyclodextrin which were rendered amorphous through non-selective alkylation. The alkylation agents suitable for that purposes are exemplified by propylene oxide, glycidol, iodoacetamide, chloroacetate, or 2-diethylaminoethylchloride; their reactions with cyclodextrins were performed in a manner to yield mixtures containing many components, a circumstance which effectively prevents crystallization processes within the above pharmaceutical preparation.

28 Claims, 2 Drawing Figures

PHARMACEUTICAL PREPARATIONS CONTAINING CYCLODEXTRIN DERIVATIVES

This application is a continuation-in-part of pending Ser. No. 603,839 filed April 25, 1984, now U.S. Pat. No. 4,596,795.

This invention comprises pharmaceutical preparations consisting generally of a drug with a substantially low water solubility and an amorphous, water-soluble cyclodextrin-based mixtures. In these preparations a stable amorphous state can be achieved and that improves the dissolution properties of the drug and hence its absorption by the body. The required cyclodextrin-based mixtures were prepared from $\alpha$-, $\beta$-, or $\gamma$-cyclodextrin which were rendered amorphous through non-selective alkylation. The alkylation agents suitable for that purpose are exemplified by propylene oxide, glycidol, iodoacetamide, chloroacetate, or 2-diethylaminoethylchloride; their reactions with cyclodextrins were performed in a manner to yield mixtures containing many components, a circumstance which effectively prevents crystallization processes within the above pharmaceutical preparation.

This method of improvement of pharmaceutical preparation comprises the addition of crystalline drugs with substantialy low solubility to compounds which have the following characteristics: (a) are water-soluble cyclodextrins, (b) have the ability to form inclusion complexes with the drugs in question, (c) are intrinsically amorphous and substantially decrease the tendency of the drug to crystallize. The above addition results in an improved solubility of the drug composition in question and more efficient absorption of the drug by the body.

The parent cyclodextrins are converted by alkylation with, e.g., epoxides or organic halides into mixtures of substituted cyclodextrins. These mixtures of cyclodextrin derivatives, after separation from contaminating products of self-condensation of epoxides or halides, are used as such, i.e., without separation into the individual cyclodextrin derivatives. Use of such water-soluble mixtures of cyclodextrin derivatives in pharmaceutical preparations enables stabilization of the amorphous state and leads to better absorption of drugs by a body.

BACKGROUND OF THE INVENTION

This invention is directed to the method of conversion of drug compositions which themselves are crystalline and of low water-solubility into intrinsically amorphous complexes which have improved pharmaceutical properties. This conversion is achieved by inclusion of the above drug compositions into water-soluble, multi-component mixtures of cyclodextrin derivatives. More particularly, the invention is related to copending application Ser. No. 603,839 which concerned cyclodextrins and sex hormones.

MATERIAL INFORMATION DISCLOSURE

Cyclodextrins are cyclic oligomers of glucose; these compounds form inclusion complexes with any drug whose molecule can fit into the lipophile-seeking cavities of the cyclodextrin molecule. Cyclodextrins are crystalline and so are their complexes with drugs, and these complexes have somewhat improved water solubilities compared to the drugs themselves. The latter improvements are the subject of reviews and of numerous patents (J. Szejtli, "Cyclodextrins and Their Inclusion Complexes," Akademiai Kiado, Budapest, 1982, pp. 204–232; J. Pitha, L. Szente, and J. Szejtli, "Molecular Encapsulation of Drugs by Cyclodextrins and Congeners," in Controlled Drug Deliver, S. D. Bruck, ed., CRC Press Inc., Boca Raton, FL, 1983, pp. 125–148).

Chemical modifications of cyclodextrins have been widely performed; with a few exceptions nevertheless the aim was preparation of another individual crystalline compound (M. L. Bender and M. Komiyama, "Cyclodextrin Chemistry," Springer-Verlag, Berlin, 1978, pp. 29–32). Condensation reactions of cyclodextrins with various epoxides or organic halides yielding compounds which are principally similar to those presently used have been known: (1) electroneutral, soluble cyclodextrin derivatives were described by Parmerter et al, U.S. Pat. No. 3,453,259, July 1969; Gramera et al, U.S. Pat. No. 3,459,731, Aug. 1969; (2) cationic, soluble cyclodextrin derivatives were described by Parmerter et al, U.S. Pat. No. 3,453,257, July 1969; and (3) insoluble, crosslinked cyclodextrins were described by Solms, U.S. Pat. No. 3,420,788, Jan. 1969. The above mixtures have not been used to obtain amorphous and water-soluble pharmaceutical preparations. Water-insoluble (crosslinked) polymers of $\beta$-cyclodextrins were previously tested as tableting additives (E. Fenyvesi, et al, Chem. Pharm. Bull., 32:665, 1984; E. Fenyvesi, et al, Chem. Pharm. Bull., 32:670, 1984). Furthermore, crosslinked $\alpha$-cyclodextrin was previously used in the preparation of sustained-release formulation of penicillin (Japanese Kokai Tokkyo Koho Patent No. 82-130914).

SUMMARY OF THE INVENTION

Dissolution properties of drugs may be improved by their conversion to an amorphous state or by complexation with cyclodextrins. The present invention combines these two improvements: described is the preparation and use of mixtures of cyclodextrin derivatives which are intrinsically amorphous, water-soluble, and capable of forming inclusion complexes with drugs. These cyclodextrin mixtures effectively solubilize lipophilic drugs into aqueous media. The solutions of these cyclodextrin mixtures are non-irritating topically and in difference to the solutions of cyclodextrins themselves do not support microbial growth. Thus, these compounds are well suited as additives/solubilizers in topical preparations. The solutions of the above cyclodextrin mixtures furthermore have very low toxicity, both systemic and local, when applied parenterally. Thus, they are well suited as additives for parenteral preparations. Furthermore, when solutions of these cyclodextrin mixtures are saturated with drugs and then evaporated or freeze-dried, solids are obtained which dissolve easily and completely and are stable for an extended period of time. These solids can be either directly tableted to yield products well suited for oral or buccal administration or processed into suppositories.

The cyclodextrin additives may be utilized in weight percent of usually about 40–60% of the drug solution composition and may be utilized from about 5–95% of the drug solution composition. Actual working models of the cyclodextrin derivatives are set out in Table 1, which shows some of the preferred as 40–50% of the drug solution composition.

TABLE 1

Solubilization of Various Drugs

| Drug | Solubility in water (mg/ml) | Solubilizer[1] (conc. in water) | Solubility (mg/ml) |
|---|---|---|---|
| acetamidophen | 11 | hydroxypropyl-β-cyclodextrin (50%) | 67.0 |
| apomorphine | 20 | hydroxypropyl-β-cyclodextrin (50%) | 116.0 |
| butylated hydroxytoluene | insoluble | hydroxypropyl-α-cyclodextrin (40%) | 0.3 |
| butylated hydroxytoluene | insoluble | hydroxypropyl-β-cyclodextrin (40%) | 3.0 |
| butylated hydroxytoluene | insoluble | hydroxypropyl-γ-cyclodextrin (40%) | 0.2 |
| chlorthalidone | 0.12 | hydroxypropyl-β-cyclodextrin (50%) | 10.5 |
| cholecalciferol | <0.23 | hydroxypropyl-β-cyclodextrin (50%) | 10.0 |
| dexamethasone | 0.1 | hydroxypropyl-β-cyclodextrin (50%) | 24.0 |
| dicumarol | <0.15 | hydroxypropyl-β-cyclodextrin (50%) | 1.3 |
| digoxin | 0.07[2] | hydroxypropyl-β-cyclodextrin (50%) | 45.0 |
| diphenylhydantoin | 0.03[2] | hydroxypropyl-β-cyclodextrin (50%) | 1.7 |
| estradiol | <1.6 | hydroxypropyl-β-cyclodextrin (40%) | 28.0 |
| estradiol | <1.6 | carboxamidomethyl-β-cyclodextrin (50%) | 25.0 |
| estradiol | <1.6 | carboxymethyl-β-cyclodextrin (50%) | 10.0 |
| estriol | <1.3 | hydroxypropyl-β-cyclodextrin (50%) | 41.0 |
| ethinylestradiol-3-methyl ether | <1.5 | hydroxypropyl-β-cyclodextrin (50%) | 27.0 |
| ethisterone | <0.2 | hydroxypropyl-β-cyclodextrin (50%) | 0.5 |
| furosemide | 0.07[2] | hydroxypropyl-β-cyclodextrin (50%) | 1.7 |
| hydroflumethiazide | 0.3 | hydroxypropyl-β-cyclodextrin (50%) | 9.3 |
| indomethacin | 0.02[2] | hydroxypropyl-β-cyclodextrin (50%) | 4.2 |
| iproniazid phosphate | 30 | hydroxypropyl-β-cyclodextrin (50%) | 95.0 |
| 17-methyltestosterone | <0.17 | hydroxypropyl-β-cyclodextrin (50%) | 39.0 |
| nitroglycerin | 1.25 | hydroxypropyl-α-cyclodextrin (40%) | 8.7 |
| nitroglycerin | 1.25 | hydroxypropyl-β-cyclodextrin[1] (40%) | 10.4 |
| nitroglycerin | 1.25 | hydroxypropyl-γ-cyclodextrin (40%) | 9.8 |
| norethindrone | 2.5 | hydroxypropyl-β-cyclodextrin (50%) | 6.8 |
| oubain | 13 | hydroxypropyl-β-cyclodextrin (50%) | 80.0 |
| oxprenolol | 127 | hydroxypropyl-β-cyclodextrin (50%) | 238.0 |
| progesterone | 0.015[3] | hydroxypropyl-β-cyclodextrin (40%) | 34.0 |
| retinal | <0.07 | hydroxypropyl-β-cyclodextrin (40%) | 2.6 |
| retinoic acid, all trans | <0.07 | hydroxypropyl-β-cyclodextrin (40%) | 0.8 |
| retinoic acid, choline salt of all trans | | hydroxypropyl-β-cyclodextrin (40%) | 18.8 |
| retinoic acid, ethanolamine salt of all trans | | hydroxypropyl-β-cyclodextrin (40%) and ethanolamine (1%) | 28.4 |
| retinoic acid, sodium salt of all trans | | hydroxypropyl-β-cyclodextrin (40%) | 1.6 |
| retinol | <0.10 | hydroxypropyl-β-cyclodextrin (40%) | 5.5 |
| spironolactone | 0.03[2] | hydroxypropyl-β-cyclodextrin (40%) | 42.0 |
| sulpiride | <0.21 | hydroxypropyl-β-cyclodextrin (50%) | 10.0 |
| testosterone | 0.026[3] | hydroxypropyl-β-cyclodextrin (40%) | 38.0 |
| testosterone | 0.026[3] | carboxamidomethyl-β-cyclodextrin (50%) | 24.0 |
| testosterone | 0.026[3] | carboxymethyl-β-cyclodextrin (50%) | 30.0 |
| theophylline | 8.3 | hydroxypropyl-β-cyclodextrin (50%) | 11.0 |
| acyclovir | insoluble | hydroxypropyl-β-cyclodextrin (50%) | 2.5 |
| cloridine hydrochloride | | hydroxypropyl-β-cyclodextrin (50%) | 83.0 |
| testosterone | 0.026[3] | dihydroxypropyl-β-cyclodextrin (40%) | 25.0 |

[1]Degrees of substitution of solubilizers used: hydroxypropyl-β-cyclodextrin and homologs, 6–7; diethylaminoethyl-β-cyclodextrin, 3.5; carboxymethyl-β-cyclodextrin, 4; carboxamidomethyl-β-cyclodextrin, 3.
[2]Data from K. Uekama, Pharmacology International, 61–65 (1985).
[3]Data from J. Brotherton, Sex Hormone Pharmacology, Academic Press, New York (1976), p. 36.

PREPARATION OF CYCLODEXTRIN MIXTURES

Suitability of cyclodextrins as pharmaceutical additives/solubilizers can be considerably improved if these are converted to mixtures of derivatives which are highly soluble and retain the capacity to form inclusion complexes with drugs. Such mixtures may be prepared by alkylation reactions which lack chemoselectivity and stereoselectivity and introduce hydrophilic substituents. In the examples are shown such alkylations.

Tables 1–3 below show solubility or dissolution of various compounds under option of cyclodextrin derivatives.

Systemic and Local Toxicity of Cyclodextrin Derivatives

Figure 1B:
FIGS. 1(A and B) shows the activity of derivatives of cyclodextrins on the forearm with a band-aid patch showing lack of topical irritation. On the left is a photograph of the forearm with band-aid patches wetted with isotonic solutions in water of AL16 (carboxamidomethyl-β-cyclodextrin), AL11 (carboxymethyl-β-cyclodextrin), M146 (hydroxypropyl-β-cyclodextrin), and SzA59/2 (diethylaminoethyl-β-cyclodextrin). On the right is the forearm after band-aids were removed after 18 hours of exposure.
Figure 1A:
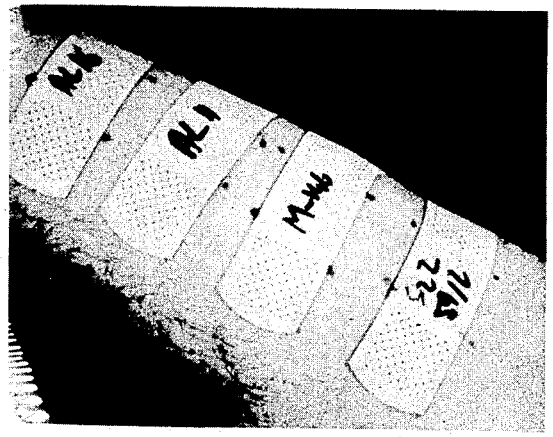

The lack of topical irritation of the above cyclodextrin derivatives was tested by wetting a band-aid with their isotonic solutions and by application of that band-aid to the forearm for about 18 hours. The representative results can be seen in FIG. 1.

The lack of parenteral toxicity of the above cyclodextrin derivatives was tested by intraperitoneal injection into mice; the following results were obtained.

(a) Two different preparations of hydroxypropyl-β-cyclodextrin were tested. The first preparation (degree of substitution 6), in doses of 10 g/kg, was without lethal effects (4 animals). The second preparation (degree of substitution 8), at 6.3 g/kg, resulted in 2 deaths (after 4 days) and 1 surviving animal; at 3.2 g/kg all 4 animals survived.

(b) Diethylaminoethyl-$\beta$-cyclodextrin at 4.7 g/kg—1 death (after 4 hrs) and 2 surviving animals; at 2.4 g/kg all 3 animals survived.

(c) Carboxymethyl-$\beta$-cyclodextrin at 3.8 g/kg—no deaths, 3 surviving animals.

(d) Carboxamidomethyl-$\beta$-cyclodextrin at 6.9 g/kg—2 deaths, 1 surviving animal; at 3.5 g/kg all 4 animals survived.

The lack of oral toxicity of hydroxypropyl-$\beta$-cyclodextrin in mice was documented in patent application Ser No. 603,839 filed April 25, 1984, by Pitha.

Dissolution Effects of Cyclodextrin Derivatives

Effectiveness of cyclodextrin derivatives in assisting dissolution of drugs is satisfactory if (a) a substantial part of the drug molecule can be fitted into the hydrophobic cavity of the cyclodextrin molecule, and (b) the same part of the drug molecule is hydrophobic. Since thee principles were established previously (see Material Information Disclosure section), the present efforts have been directed to dividing drugs into categories according to their steric bulk and documenting the usefulness of the present method for a few representatives of every category.

Improved Absorption of Drugs from the Preparations Described Above

The principal improvement of absorption of a drug by a body accompanying the conversion of a drug from a crystalline state into an amorphous state is generally recognized.

TABLE 2

Solubilities of Steroids (mg/ml) in 50% Aqueous Solutions of Hydroxypropyl-$\beta$-cyclodextrin Samples With Different Degrees of Substitution (d.s.)

| | d.s. 4.7 | d.s. 5.7 | d.s. 7.0 | d.s. 14 |
|---|---|---|---|---|
| Estradiol | 30 | 35 | 26 | 18 |
| Progesterone | 30 | 44 | 35 | 23 |
| Testosterone | 56 | 62 | 40 | 23 |

TABLE 3

Solubilities of Steroids (mg/ml) in 50% Aqueous Solutions of Substituted Cyclodextrins

| | Carboxamido-$\beta$-cyclodextrin | Diethylaminoethyl-$\beta$-cyclodextrin | Carboxymethyl $\beta$-cyclodextrin |
|---|---|---|---|
| Estradiol | 28 | 8 | 14 |
| Progesterone | 38 | 18 | 14 |
| Testosterone | 24 | 9 | 24 |

EXAMPLE 1

Preparation of hydroxypropyl-$\beta$-cyclodextrin

Sodium hydroxide (105.7 g, 2.64 moles) was dissolved in 750 ml of distilled water and to this solution was added $\beta$-cyclodextrin (346.4 g of commercial preparation containing 13.4% of water; i.e., 300 g of anhydrous compound corresponding to 0.264 moles). Suspension was stirred at 60° C. until all $\gamma$-cyclodextrin was dissolved. Thereafter solution was cooled to room temperature and reflux condenser, filled with dry ice-acetone mixture, was attached. Then propylene oxide (redistilled; 185 ml; i.e., 153.5 g corresponding to 2.64 moles) was added, in fast manner but with necessary cautions, to the stirred solution. After addition of propylene oxide, the solution was stirred overnight at room temperature. Thereafter, the alkaline solution was neutralized by concentrated hydrochloric acid and evaporated in vacuo to the consistency of thick syrup. The syrup was dissolved in ethanol (1.5 L) and left standing to precipitate sodium chloride which was subsequently filtered off. The ethanolic solution was evaporated in vacuo and the rest was dissolved in water. The solution was enclosed in dialysis tubing and dialyzed for 2-3 hours against water. The dialyzed solution was then clarified by centrifugation and freeze-dried. The resulting white powder (282 g) contained 5.2% water (measured by weight loss), 0.65% of inorganic residue (by ashing), and 0.87% of chloride (elementary analysis). Upon prolonged standing water content increased to 7-8% but appearance of the compound (white powder) was not changed. By prolonged trituration of this powder with acetone, the products of self-condensation of propylene oxide, which contaminate the desired hydroxypropyl- $\beta$-cyclodextrin, can be removed. The degree of substitution of the cyclodextrin moiety achieved in the above reaction was about 7; by variation of the amounts of reagents the substitution degrees were manipulated. Further or alternative purification of hydroxypropyl-$\beta$-cyclodextrin consisted in the preparation of clear solutions of the raw material in water or ethanol and addition of large volumes of a nonpolar solvent (e.g., acetone) which precipitated the desired solid hydroxypropyl-$\beta$-cyclodextrin, whereas highly substituted cyclodextrins and products of self-condensation of propylene oxide remained in the solution from which they can be recovered by evaporation, leaving oily liquid. In a representative experiment, precipitation yielded 81% of the desired solid hydroxypropyl-$\beta$-cyclodextrin (degree of substitution 7 by nuclear magnetic resonance and 8.02 by mass spectroscopy) and 18% of oily liquid containing also hydroxypropyl-$\beta$-cyclodextrin (degree of substitution 16 by nuclear magnetic resonance and 11 3 by mass spectrometry). When condensation of propylene oxide with $\gamma$-cyclodextrin was performed with a high ratio of the former to the latter, products were precipitable by cyclohexane but not by acetone and were semi-solid liquids (degree of substitution 14 by nuclear magnetic resonance).

EXAMPLE 2

Related preparations: O-alkylation of cyclodextrins with epoxides

Basically the same conditions as above were used also for condensation of $\alpha$- or $\gamma$-cyclodextrins with propylene oxide; degrees of substitution achieved (by nuclear magnetic resonance) were close to those described above.

EXAMPLE 3

Related preparations: O-alkylation of cyclodextrins with organic halides.

The procedures analogous to those above were also used for condensation of $\beta$-cyclodextrin with the following hydrophilic alkylating agents: (a) diethylaminoethylchloride-hydrochloride yielding diethylaminoethyl- $\beta$-cyclodextrin; the degree of substitution in the product was about 3.5 (calculated from nitrogen content), (b) chloroacetic acid yielding carboxymethyl-$\beta$-cyclodextrin; the degree of substitution in the product was about 4 (calculated from sodium content), (c) iodoacetamide yielding carboxamidomethyl- $\beta$- cyclodextrin; the degree of substitution in the product was about 3 (calculated from nitrogen content).

EXAMPLE 4

The solutions of solubilizer in water were saturated by stirring with excess of drug at room temperature for about 24 hours. The resulting suspensions were clarified either by filtration through a sintered glass filter or by centrifugation. Concentration of hormones in clarified solutions was measured spectrophotometrically. Representative results are given in Table 1, ante. In these experiments drugs were solubilized with cyclodextrin derivatives with constant degrees of substitution and which are given in the footnote to Table 1. In Table 2 are the results on the solubilization of sex hormones with hydroxypropyl-β-cyclodextrin samples of different degrees of substitution. It is apparent that samples of hydroxypropyl-β-cyclodextrin with medium degrees of substitution (5-7) are more effective solubilizers than those of higher degrees of substitution. It should be noted that while the former derivatives are solid and suitable for tableting purposes, the latter are semisolids or liquids. The results on the solubilization of sex hormones by cyclodextrin derivatives containing carboxamido or diethylaminoethyl or carboxymethyl substituents are summarized in Table 3. It is apparent that the carboxamido methyl derivative is a relatively potent solubilizer; nevertheless, comparison with the results in Table 2 show that the potency of hydroxypropyl containing derivatives has not been surpassed.

EXAMPLE 5

The above solutions of drugs in cyclodextrin derivatives were stable when kept at room temperature for several months and no microbial growth on the solutions was observed. When freeze-dried, the solutions which were prepared using solid derivatives of cyclodextrins again yielded non-hygroscopic, stable powders which were found suitable for tableting by direct compression. The tablets prepared in such a manner again dissolved completely in water as documented by Example 6.

EXAMPLE 6

Figure 2:
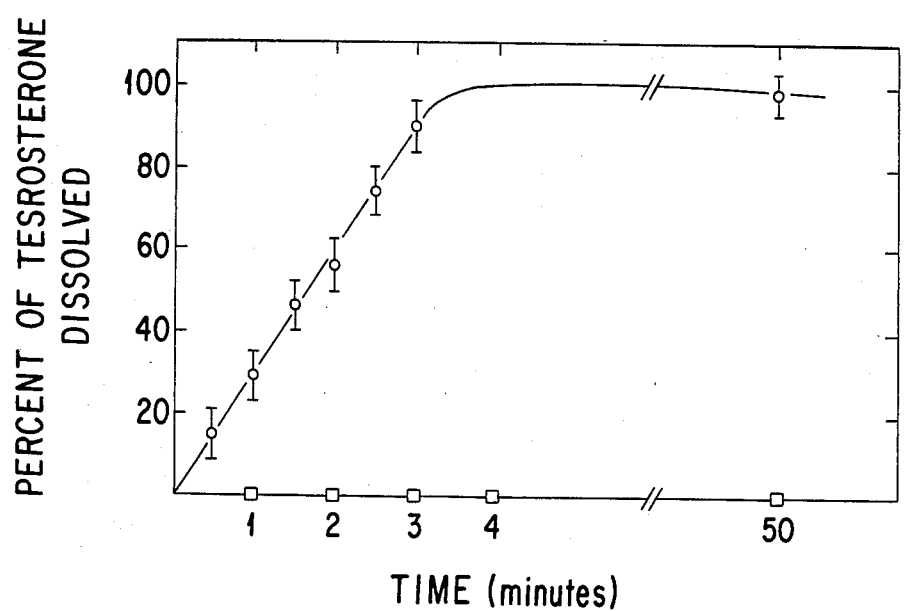
FIG. 2 shows the dissolution of testosterone from a tablet made from testosterone/hydroxypropyl-β-cyclodextrin complex (—0—) or from a tablet made from testosterone-microcrystalline cellulose (—□—).

Using a die of 0.9 cm diameter and a force of 3000 pounds weight exerted in a single-station hand-operated unit, the tablets were made directly from the freeze-dried solutions of drugs prepared as described above. In one such experiment tablets weighing about 130 mg and containing 10 mg of testosterone in complexed form were made. These tablets were stored for up to 16 months at room temperature in a well-closed glass container without any deterioration and were thereafter tested for dissolution properties. In the dissolution experiments a tablet was submerged in a basket made out of stainless steel mesh in a bath of water, at 20 C and sink conditions. As noted in FIG. 2, the complexed testosterone tablets dissolved completely with 4 minutes, whereas similar tablets prepared from testosterone and microcrystalline cellulose did not release practically any testosterone into the aqueous phase.

Definitions

The term "mixture of substituted amorphous cyclodextrins" is directed towards where there is more than one cyclodextrin and where there is more than one degree of substitution which will vary from a preferred range of about 3 to about 7.

I claim:

1. A method of producing a stablizing amorphous complex of a drug and a mixture of cyclodextrins which comprises the steps of:
   1. Dissolving an intrinsically amorphous mixture of cyclodextrin deratives which are water soluble and capable of forming inclusion complexes with drugs in water; and
   2. Solublizing lipophilic drugs into the aqueous media to form a solution and form a solublized drug/cyclodextrin complex.
2. A method of claim 1 wherein the solubilized complex is subjected to freeze-dried or evaporation to provide a solid cyclodextrin/drug complex in powder form.
3. A method of claim 1 wherein cyclodextrins used are substituted by at least one of the following substituents: hydroalkyl, carboxamide, diethylaminoethyl, carboxymethyl, and carboxyamidomethyl.
4. A method of claim 1 wherein the drug is a hormone.
5. A method of claim 4 wherein the drug is testosterone, an estrogen, or a progesterone.
6. A composition of matter which contains an amorphous complex of cylodextrin and a drug.
7. A omposition of matter of claim 6 wherein the drug is a hormone.
8. A composition of claim 6 wherein the drug is at least one of testosterone, progesterone, and an estrogenic drug.
9. A composition of matter of claim 6 in solid form.
10. A composition of matter of claim 9 which is a tablet.
11. A composition of matter of claim 6 which is in a liquid or semi-liquid form.
12. A composition of matter for use in the process of claim 1 containing a mixture of substituted cyclodextrin derivatives in amorphous form.
13. A composition of matter of claim 6 wherein the drug is a vitamin.
14. A composition of matter of claim 6 wherein the drug is a salt of retinoic acid.
15. A composition of matter of claim 6 wherein the drug is a steroid.
16. A composition of matter of claim 6 wherein the drug is a spironolactone.
17. A composition of matter of claim 6 wherein the drug is an antiviral agent.
18. A composition of matter of claim 17 wherein the antiviral agent is acylovir.
19. A composition of matter of claim 6 wherein the drug is a diuretic.
20. A composition of matter of claim 19 wherein the diuretic is chlorthalidone.
21. A composition of matter of claim 6 wherein the drug is an anticoagulant.
22. A composition of matter of claim 21 wherein the anticoagulant is dicumerol.
23. A composition of matter of claim 6 wherein the drug is an anticonvulsant
24. A composition of matter of claim 23 wherein the drug is diphenylhydantoin.
25. A composition of matter of claim 6 wherein the drug is an antiinflammatory agent.
26. A composition of matter of claim 25 wherein the antiinflammatory agent is iproniazid.
27. A composition of matter of claim 16 wherein the drug is oxyprenolol.
28. A composition of matter in solid or semi-solid form comprising at least one of testosterone, progesterone, and estradiol as an inclusion complex with poly-β-cylodextin and/or hydroxypropyl-β-cyclodextrin adapted for administration by buccal route.

* * * * *

UNITED STATES PATENT AND TRADEMARK OFFICE
CERTIFICATE OF CORRECTION

PATENT NO. : 4,727,064

DATED : February 23, 1988

INVENTOR(S) : Pitha, Josef

It is certified that error appears in the above-identified patent and that said Letters Patent is hereby corrected as shown below:

Claim 1, line 1, change "stabilizing" to --stabilized--

Claim 2, line 2, change "freeze-dried" to --freeze-drying--

Claim 3, line 3, change "hydroalkyl" to --hydroxyalkyl--

Claim 7, line 1, change "omposition" to --composition--

Signed and Sealed this

Thirty-first Day of January, 1989

*Attest:*

DONALD J. QUIGG

*Attesting Officer*   *Commissioner of Patents and Trademarks*